United States Patent
Slavtcheff et al.

(10) Patent No.: US 6,506,713 B1
(45) Date of Patent: Jan. 14, 2003

(54) COSMETIC EFFERVESCENT CLEANSING COMPOSITIONS

(75) Inventors: Craig Stephen Slavtcheff, Guilford, CT (US); Robert Edward Gott, Norwalk, CT (US); Alexander Paul Znaiden, Trumbull, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 26 days.

(21) Appl. No.: 09/635,377

(22) Filed: Aug. 9, 2000

Related U.S. Application Data
(60) Provisional application No. 60/179,235, filed on Jan. 31, 2000.

(51) Int. Cl.[7] .................................................. A61K 7/50
(52) U.S. Cl. ....................... 510/130; 510/139; 510/297; 510/439; 424/401; 424/402; 424/404
(58) Field of Search ................................. 510/130, 139, 510/439, 140; 424/404, 401, 402

(56) References Cited

U.S. PATENT DOCUMENTS

| | | | |
|---|---|---|---|
| 1,808,834 A | 6/1931 | Busch |
| 4,234,442 A | 11/1980 | Cornelissens |
| 4,272,393 A | 6/1981 | Gergely |
| 4,515,703 A | 5/1985 | Haq |
| 4,600,620 A | 7/1986 | Lloyd et al. |
| 4,666,707 A | 5/1987 | Eguchi et al. |
| 6,063,390 A | 5/2000 | Farrell et al. |

FOREIGN PATENT DOCUMENTS

| | | |
|---|---|---|
| WO | 97/43366 | 11/1997 |
| WO | 99/48469 | 9/1999 |

*Primary Examiner*—Necholus Ogden
(74) *Attorney, Agent, or Firm*—Milton L. Honig

(57) ABSTRACT

A cosmetic cleansing article is provided which includes an effervescent cleanser composition held within a sachet having at least one water permeable wall. The effervescent composition is an intimate mixture of an acid material such as citric acid and an alkaline material such as sodium bicarbonate. Water contact causes the combination to effervesce. The powdered mixture of alkaline/acid materials is storage stabilized against premature effervescent action by dispersing therewithin plant solids.

10 Claims, No Drawings

COSMETIC EFFERVESCENT CLEANSING COMPOSITIONS

This application claims the benefit of Ser. No. 60/179,235, filed Jan. 31, 2000.

BACKGROUND OF THE INVENTION

1. Field of the Invention

The invention concerns an effervescent foaming composition in a storage stabilized dry form, the composition preferably being applied for body cleansing and delivered within a water permeable sachet.

2. The Related Art

Classically the process of cleansing skin or other substrates has employed a surfactant composition. Sometimes an implement has joined the composition. Implements such as sachets serve a multi-purpose. One function is as a delivery package for the surfactant. Sachets may also assist in generating foam. They also function as an abrasive assisting in the cleansing function.

An early example of cleansing pad technology is found in U.S. Pat. No. 1,808,834 (Busch Sr.). A fabric pouch is disclosed surrounding a cleansing composition mainly consisting of calcium and sodium carbonate.

U.S. Pat. No. 4,234,442 (Cornelissens) describes a sachet which can consist of a water permeable material filled with an acidic and an alkaline constituent. Adipic, succinic and glutaric acids exemplify the acidic constituent. Sodium bicarbonate and carbonate represent the alkaline ingredient.

U.S. Pat. No. 4,272,393 (Gergely) describes a cleaning article formed of a porous flexible substrate, especially a cellulosic paper, impregnated with detergent and a gas-generating system. The latter is formed by separating an acidic component such as citric acid from a basic component such as sodium carbonate in two separate areas of the substrate.

U.S. Pat. No. 4,515,703 (Haq), U.S. Pat. No. 4,600,620 (Lloyd et al.) and U.S. Pat. No. 4,603,069 (Haq et al.) all describe wiping articles impregnated with surfactant. These do not contain any effervescent ingredients.

WO 97/43366 (Askew et al.) reports an effervescent system to improve dispensability of granular laundry detergent powders into wash water of automatic washing machines. Citric acid and bicarbonate combinations are employed to generate effervescence.

WO 99/48469 (Yagnik et al.) discloses powdered compositions some of which may be delivered via a tea bag. These compositions are formulated with an exothermic ingredient, a pH adjusting agent such as citric acid, optionally sodium bicarbonate for an effervescent effect and an aromatic ingredient for fragrance.

Common to those of the aforementioned systems employing effervescent anhydrous powders is the need to maintain them in a dry state under storage conditions. Seepage of atmospheric moisture into the powders will prematurely activate effervescence.

Accordingly, it is an object of the present invention to stabilize against premature activation a powdered effervescent cleanser composition.

Another object of the present invention is to provide a powdered system for effervescing wherein the powders are stabilized against caking.

Yet another object of the present invention is to provide a cleansing article such as a sachet containing an effervescent system which upon being activated by water generates carbon dioxide to enhance the lathering of cleanser components.

Still a further object of the invention is to provide a cleansing article which imparts a pleasant sensory feel to skin during and after use.

It is to be noted that the subsequently described invention is broader than the objects or technical problems it is directed to solve.

SUMMARY OF THE INVENTION

A cosmetic article is provided for cleansing body surfaces, the article including:

- a sachet having at least one water permeable wall, the sachet being sealed along its perimeter; and
- an effervescent cleanser composition in the form of an anhydrous dry solid being positioned within the sachet, the composition including:
  - (i) from about 1 to about 80% of an alkaline material;
  - (ii) from about 0.5 to about 80% of an acid material; and
  - (iii) from about 0.1 to about 80% of dried plant solids.

Also provided is a method for cleansing skin involving wetting with water a cosmetic article containing the effervescent composition delineated above, generating foam from the article and contacting skin surfaces with the generated foam, particularly in the context of bathing.

DETAILED DESCRIPTION OF THE INVENTION

Now it has been found that dried plant solids can be interspersed with a powdered composition of alkaline material and acid material to act as a stabilizing agent against premature activation of effervescence. Plant solids of almost any description can be employed. These solids will be in particle form having sizes ranging from about 1 mm to about 40 mm in length, and of comparable width. Preferably, the solids will have particle sizes ranging from about 5 mm to about 25 mm, more preferably from about 10 mm to about 15 mm. So long as they are dried, most any portion of a plant may be employed including stems, flowers and leaves. Leaves are most desirable. Amounts of the plant solids will range from about 0.1 to about 80%, preferably from 5 to 50%, optimally from about 10 to about 30% by weight.

Non-limiting examples of plant solids may include herbs, teas (e.g. green, black and oolong tea) and potpourri. Among suitable plant solids are those derived from the leaves, flowers, stems and roots of such botanicals as wintergreen, bay (leaves) cocoa, eucalyptus, cotton, biti, lemongrass, lily, spanish moss, rosemary, parsley, tarragon, angelica, basil, hops, oregano, thyme, zatar, ginseng, willow, poplar, dandelion, comfrey and combinations thereof. These solids need not be fragrance emitting, and indeed it is preferred to add aroma chemicals separate from the plant solids. In a preferred embodiment, the aroma chemicals and fragrances are sprayed onto a solid substrate, preferably a polysaccharide, and the mixture then incorporated with the alkaline and acid powdered materials.

Cosmetic wiping articles of the present invention when contacted with water billow to many times (more than 10 but often more than 40 times) their dry size when activated by water. The effervescent cleansing system exudes copious amounts of lather. A plumped "pillow" arises from the effervescent action. By careful control of the acidic and alkaline components, a squeaky clean rinsed feeling is felt on a user's skin.

An important component of compositions within the sachet is that of an acidic material. Suitable for this purpose are any acids present in dry solid form. Especially appropriate are $C_2$–$C_{20}$ organic mono- and poly-carboxylic acids and especially alpha- and beta-hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

Another important component of compositions within the sachet is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

By the term "anhydrous" is meant the presence of no more than 5%, preferably no more than 3.5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

Advantageously but not necessarily compositions can include a surfactant, preferably, a dry surfactant solid at 20° C. Most suitable for the present invention is sodium cocoyl isethionate. Other useful surfactants include sodium methyl cocoyl taurate and sodium lauryl sulfate. Surfactants may be of the anionic, cationic, nonionic, amphoteric, zwitterionic varieties and combinations thereof. Amounts of the dry surfactant may range from about 0.1 to about 30%, preferably from about 1 to about 30%, optimally from about 8 to about 15% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. sodium bicarbonate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 30%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid ester, diethylene glycol mono- and di-fatty acid esters, polyethylene glycol (200–6000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

(6) Triglycerides such as sunflower seed oil, maleated sunflower seed oil, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, riconleic, arachidic, behenic and erucic acids.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, tricloban, hexetidene, chlorhexadene, gluconates, zinc salts (e.g. zinc citrate and zinc phenolsulfonate) and combinations thereof.

Skin lighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose. Most preferred for purposes of this invention are cationic guar gums such as Jaguar C13S® which is guar hydroxypropyltrimonium chloride. Amounts of the deposition aid may range from about 0.01 to about 1%, preferably from about 0.05 to about 0.5%, optimally from about 0.1 about 0.3% by weight.

Advantageously an emotive agent such as a fragrance and/or botanical extract are included with the effervescent cleansing composition. Fragrances and botanicals are often liquids. For this reason it is necessary to uniformly distribute and allow absorption of liquid components into the solid powder. One method of best achieving this is to spray these liquids onto the solids. Amounts of the fragrance and/or botanicals combined may be at levels from 0.1 to 3%, preferably from 0.5 to 2%, optimally from 0.8 to 1.5% by weight of the total composition.

The terms "fragrance" and "botanical extract" are defined as mixtures of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units. Examples include alpha and beta pinene, myrcene, geranyl alcohol and acetate, camphene, dl-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof. Botanical extracts of particular use in the present invention include those extracted from yarrow, chamomile, jasmine, lavender, horse chestnut, sage, thyme, yucca, coltsfoot and mixtures thereof.

Preservatives can desirably be incorporated into the cosmetic compositions of this invention to protect against the growth of potentially harmful microorganisms. Particularly preferred preservatives are phenoxyethanol, methyl paraben, propyl paraben, imidazolidinyl urea, sodium dehydroacetate and benzyl alcohol. The preservatives should be selected having regard for the sue of the composition and possible incompatibilities between the preservatives and other ingredients in the emulsion. Preservatives are preferably employed in amounts ranging from 0.01% to 2% by weight of the composition.

Colorants may also be included in compositions of the present invention. These substances may range from about 0.05 to about 5%, preferably between 0.1 and 3% by weight.

Effervescent cleansing compositions of this invention will be placed within a sachet. Preferably the sachet is constructed from a first and second substrate sheet. At least one of the sheets must be water permeable, most preferably both sheets should have water permeability. For definitional purposes, first and second sheets can be folded-over panels of a single unitary sheet. Suitable materials for forming sheets may be rayon, polyester, polyethylene, polypropylene, cotton or any combination thereof. These sheets may be woven or non-woven. Most preferred is a non-woven rayon. Cellulosic paper fiber substrates are best not employed because of their insufficient wet-strength although they may be blended with other fibers referenced above; it is important that the substrate sheets are not readily torn open through consumer rubbing of the article. Unlike laundry sachet articles, sachets of the present invention should not rupture to allow dispersion of their granular contents into wash water. Rather it is intended for all cleanser composition components to exit by dissolution through the permeable walls of the sachet. Advantageously at least one of the sheets should be sufficiently translucent to allow viewing from outside of the ingredients. A calendered pattern helps achieve a translucent panel while still retaining strength and water permeability. Sachets may have any geometric shape including square, round, oval and tetrahedral configurations.

Skin surfaces against which articles of the present invention are useful include face, body, scalp, axilla and even legs/feet. When the article is a foot cleanser, it would be advantageous for the sachet on one of its sides to be coarse while the second of the sheets may be soft and gentle. An abrasive non-woven flexible sheet in a foot cleanser product is useful for rubbing against calluses while the second sheet of the sachet remains smooth.

Articles according to the present invention may be formed in a variety of ways. An illustrative but certainly non-limiting example is as follows. Constituents of the effervescent cleansing composition other than the plant solids are placed into a dry mill or similar apparatus and blended until a uniformly distributed powder results. Liquid fragrance is sprayed onto a polysaccharide powder which in turn is added to the dry mill with concurrent agitation of the powdered composition. Sachets are formed of water permeable rayon/polyester walls in the form of a tetrahedron having three of its sides sealed, leaving an open top side. Plant solids are then added to the sachet through the open side. Subsequently, the effervescent composition is charged into the sachet and the latter sealed shut by heat bonding.

Ultrasonic welding may be employed as an alternative to heat-sealing. Thread stitching, glue application or other closure mechanisms may also be utilized.

Except in the operating and comparative examples, or where otherwise explicitly indicated, all numbers in this description indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

All measurements referred to herein are made at 25° C. unless otherwise specified. All publications, patent applications and issued patents mentioned herein are hereby incorporated in their entirety by reference. Citation of any reference is not an admission regarding any determination as to its availability as prior art to the claimed invention.

The following examples will more fully illustrate embodiments of this invention. All parts, percentages and proportions referred to herein and in the appended claims are by weight unless otherwise indicated.

EXAMPLE 1

An effervescent cleansing composition is prepared according to the formulation reported in Table I. Phase A is dry blended in a high speed shearing mixer. Fragrance is then sprayed onto the resultant powder as a Phase B. Thirty grams of the resultant powder are then mixed with ten grams of bay leaves, the combination being placed into a sachet formed of non-woven spun bond polyester. All sides are closed by double stitching with thread.

TABLE I

| INGREDIENT | WEIGHT % |
|---|---|
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |

EXAMPLE 2

Another effervescent cleansing composition is prepared according to the formulation reported in Table II. Twenty grams of the resultant powdered formulation is then mixed with twenty grams of basil leaves. This combination is then sealed within a sachet.

TABLE II

| INGREDIENT | WEIGHT % |
|---|---|
| PHASE A | |
| Sodium Bicarbonate | 32.3 |
| Citric Acid (Anhydrous) | 41.1 |
| Sodium Cocyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| Laracare A200 ® (Arabinogalactan) | 1.0 |
| Ascorbic Acid | 0.5 |
| PHASE B | |
| Fragrance | 1.0 |

EXAMPLE 3

A face cleansing effervescent composition is prepared according to the formulation reported in Table III. Thirty-five grams of the resultant powdered formulation are mixed with five grams of lemongrass leaves/stems. The combination is then sealed within a sachet.

TABLE III

| INGREDIENT | WEIGHT % |
|---|---|
| PHASE A | |
| Sodium Bicarbonate | 33.6 |
| Citric Acid (Anhydrous) | 39.0 |
| Sodium Cocyl Isethionate (Powder) | 3.0 |
| Sodium Methyl Cocoyl Taurate | 6.0 |
| Cocoamidopropylbetaine | 2.5 |
| Sodium Sesquicarbonate | 5.0 |
| Lipothix 100B ® (Potassium Polymetaphosphate/Bicarbonate 70:30) | 0.5 |

TABLE III-continued

| INGREDIENT | WEIGHT % |
|---|---|
| Optigel SH ® (Sodium Magnesium Silicate) | 2.0 |
| Tapioca | 5.5 |
| Methyl Gluceth 20-Benzoate | 2.0 |
| Guar Hydroxypropyl Trimonium Chloride | 0.25 |
| PHASE B | |
| Fragrance | 0.65 |

EXAMPLE 4

A still further effervescent cleansing composition according to the present invention may be prepared according to the formulation reported under Table IV. Phase A is prepared by dry mixing of the ingredients in a high speed shear mixer. Thirty grams of resultant powder are then mixed at low shear with ten grams of green tea leaves. The combination is placed into a sachet formed of non-woven cotton polyester (50:50). The mesh size of the pouch walls is sufficient to allow transfer of dissolved ingredients. All sides of the sachet are welded by ultrasonic heat to insure against powder escaping from the pouch.

TABLE IV

| INGREDIENT | WEIGHT % |
|---|---|
| PHASE A | |
| Potassium Bicarbonate | 29.5 |
| Lactic Acid (Anhydrous) | 45.4 |
| Sodium Sulfosuccinate | 11.6 |
| Sodium Sesquicarbonate | 5.0 |
| Lipothix 100B ® (Potassium Polymetaphosphate/Bicarbonate 70:30) | 0.5 |
| Optigel SH ® Sodium Magnesium Silicate | 1.0 |
| Kelacid ® (Alginic Acid) | 1.0 |
| Sorbitol | 5.0 |
| PHASE B | |
| Fragrance | 1.0 |
| Licorice Extract | 0.1 |

EXAMPLE 5

Still another effervescent cleansing composition is prepared according to the formulation reported in Table V. The ingredients are dry blended in a high speed shearing mixer. Fragrance and herbal extract are sprayed onto the powder and further blended to achieve homogeneity. Twenty grams of the resultant powder are admixed with twenty grams of chamomile tea leaves and placed within a sachet formed of non-woven polypropylene. All sides are closed by convection heat sealing along the perimeter thereof.

TABLE V

| INGREDIENT | WEIGHT % |
|---|---|
| PHASE A | |
| Sodium Bicarbonate | 29.5 |
| Citraconic Acid (Anhydrous) | 45.4 |
| Methyl Glucamide | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |

TABLE V-continued

| INGREDIENT | WEIGHT % |
|---|---|
| Kelacid ® (Alginic Acid) | 1.0 |
| Sorbitol | 5.0 |
| PHASE B | |
| Fragrance | 0.9 |
| Yarrow | 0.1 |

EXAMPLE 6

An effervescent cleansing composition according to the present invention was prepared according to the formulation reported under Table VI. The composition of Table VI was placed in a set of sachets as control samples. A second set of samples was prepared similar to the control but in addition to the 30 gram cleansing composition charge, an additional 10 grams of wintergreen leaves were mixed into the formulation. All sachets were then placed in an oven at 50□C for three weeks.

Control samples were evaluated after the storage test. All were found to be caked indicating water absorption. None of the sachets formulated with wintergreen leaves had caked contents. They all remained flowable powders within the sachets indicating no water absorption. Thus, the wintergreen leaves allowed the effervescent composition to retain full activity for use in a bath.

TABLE VI

| INGREDIENT | WEIGHT % |
|---|---|
| PHASE A | |
| Citric Acid (Anhydrous) | 33.00 |
| Sodium Bicarbonate | 30.00 |
| Sodium Sesquicarbonate | 17.42 |
| Pentasodium Triphosphate | 6.96 |
| Cocoamidopropylbetaine | 1.05 |
| Maltodextrin | 9.00 |
| Water dispersible titanium dioxide | 0.60 |
| Colorant* | 0.37 |
| PHASE B | |
| Fragrance | 1.60 |

*0.667% FD&C Blue 1, 0.133% FD&C Yellow 10, 66% polypropylene glycol and 33.3% water

EXAMPLE 7

A consumer study was conducted to evaluate performance of sachet based articles of the present invention with those of effervescent tablets of similar composition. The sachet products in the study were formulated similar to that found under Table VI and contained herbal dried plant solids.

Women panelists aged 18 to 64 participated. Panelists used the product at least twice during a one-week period in a bath. After use of the products, the panelists were requested to complete a questionnaire on their experiences. Table VII reports results from the questionnaire. Only those questions eliciting a statistical significance at 95% confidence level are recorded in the Table.

TABLE VII

| QUESTION | EFFERVESCENT TABLET (46 PANELISTS) | SACHET (51 PANELISTS) |
|---|---|---|
| Initially having an attractive appearance when effervescing | | |
| Top two boxes | 54 | 55 |
| Excellent | 15 | 33* |
| Very Good | 39 | 22 |
| Good | 33 | 24 |
| Fair | 9 | 15 |
| Poor | 4 | 6 |
| Is a unique product | | |
| Top two boxes | 44 | 70* |
| Excellent | 18 | 35 |
| Very Good | 26 | 35 |
| Good | 26 | 14 |
| Fair | 26 | 12 |
| Poor | 4 | 4 |
| Color change of the water | | |
| Top two boxes | 19 | 39* |
| Excellent | 2 | 8 |
| Very Good | 17 | 31 |
| Good | 33 | 37 |
| Fair | 22 | 16 |
| Poor | 26 | 8 |
| After using the product, skin felt . . . | | |
| Top two boxes | 55 | 59 |
| Very moisturized | 9 | 30* |
| Somewhat moisturized | 46 | 29 |
| Neither | 39 | 37 |
| Somewhat dry | 6 | 4 |
| Very dry | 0 | 0 |
| Continuously emits a fragrance | | |
| Top two boxes | 40 | 70* |
| Agree Strongly | 17 | 29 |
| Agree Somewhat | 33 | 41 |
| Neither Agree nor Disagree | 13 | 8 |
| Disagree Somewhat | 13 | 10 |
| Disagree Strongly | 24 | 12 |
| Helps you to relax | | |
| Top two boxes | 41 | 61* |
| Agree Strongly | 15 | 20 |
| Agree Somewhat | 26 | 41 |
| Neither Agree nor Disagree | 26 | 22 |
| Disagree Somewhat | 11 | 10 |
| Disagree Strongly | 22 | 7 |
| Water has a pleasant appearance | | |
| Top two boxes | 48 | 69* |
| Agree Strongly | 13 | 28 |
| Agree Somewhat | 35 | 41 |
| Neither Agree nor Disagree | 24 | 20 |
| Disagree Somewhat | 15 | 4 |
| Disagree Strongly | 13 | 7 |

The foregoing description and examples illustrate selected embodiments of the present invention. In light thereof variations and modifications will be suggested to one skilled in the art, all of which are within the spirit and purview of this invention.

What is claimed is:

1. A cosmetic article for cleansing body surfaces, the article comprising:
    a sachet having at least one water permeable wall, the sachet being sealed along its perimeter; and
    an effervescent cleanser composition in the form of an anhydrous dry solid being positioned within the sachet, the composition comprising:
        (i) from about 1 to about 80% of an alkaline material;
        (ii) from about 0.5 to about 80% of an acid material; and
        (iii) from about 0.1 to about 80% of dried plant solids in the form selected from the group consisting of stems, flowers, leaves and mixtures thereof.

2. The article according to claim 1 wherein the composition further comprises from about 0.01 to about 30% by weight of a skin benefit agent selected from the group consisting of emollients, anti-aging actives, antibacterials and fungicides, skin lighteners, sunscreens and mixtures thereof.

3. The article according to claim 1 wherein the plant solids have a particle size ranging from about 1 mm to about 40 mm in length and width.

4. The article according to claim 1 wherein the composition further comprises from about 0.1 to about 3% by weight of an emotive agent selected from the group consisting of liquid fragrance, botanical extract and mixtures thereof.

5. The article according to claim 4 wherein the emotive agent is incorporated into the composition by spray application onto one or more other powdered components of the composition.

6. The article according to claim 1 wherein the alkaline material is a bicarbonate or carbonate salt.

7. The article according to claim 1 wherein the composition further comprises a surfactant in an amount from about 0.1 to about 30% by weight.

8. The article according to claim 1 wherein the acid material is citric acid.

9. The article according to claim 1 wherein the composition further comprises from about 0.01 to about 1% by weight of a deposition aid which is a cationic monomer or polymer.

10. A method for cleansing skin comprising wetting an effervescent cleansing article, generating foam from the article and contacting skin surfaces with the generated foam, the article comprising:
    a sachet having at least one water permeable wall, the sachet being sealed along all its perimeter; and
    an effervescent cleanser composition in the form of an anhydrous dry solid being positioned within the pouch, the composition comprising:
    (i) from about 1 to about 80% of an alkaline material
    (ii) from about 0.5 to about 80% of an acid material; and
    (iii) from about 0.1 to about 80% of dried plant solids in the form selected from the group consisting of stems, flowers, leaves and mixtures thereof.

* * * * *